United States Patent
Aida et al.

(10) Patent No.: US 10,030,155 B2
(45) Date of Patent: Jul. 24, 2018

(54) GRAPHENE NANODISPERSION AND METHOD FOR PREPARING SAME

(71) Applicant: The University of Tokyo, Tokyo (JP)

(72) Inventors: Takuzo Aida, Tokyo (JP); Chiyoung Park, Tokyo (JP); Saisuwan Ravi, Tokyo (JP); Michio Matsumoto, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 248 days.

(21) Appl. No.: 14/400,877

(22) PCT Filed: May 14, 2013

(86) PCT No.: PCT/JP2013/063438
§ 371 (c)(1),
(2) Date: Nov. 13, 2014

(87) PCT Pub. No.: WO2013/172350
PCT Pub. Date: Nov. 21, 2013

(65) Prior Publication Data
US 2015/0137027 A1  May 21, 2015

(30) Foreign Application Priority Data

May 14, 2012  (JP) .................................. 2012-111019
Mar. 22, 2013  (JP) .................................. 2013-060376

(51) Int. Cl.
*C07D 403/14* (2006.01)
*C01B 32/182* (2017.01)
(Continued)

(52) U.S. Cl.
CPC .............. *C09D 5/24* (2013.01); *B01F 3/1235* (2013.01); *B01F 9/0003* (2013.01); *B01F 11/02* (2013.01);
(Continued)

(58) Field of Classification Search
CPC ... C07C 211/09; C07D 401/12; C07D 403/02; C07D 233/64; C07D 403/14; H01B 1/02;
(Continued)

(56) References Cited

U.S. PATENT DOCUMENTS 3,911,133 A * 10/1975 Edwards .............. A61K 8/4946
424/54
2005/0156144 A1  7/2005 Fukushima et al.
(Continued)

FOREIGN PATENT DOCUMENTS

CN  101049575 A  10/2007
CN  101781254 A  7/2010
(Continued)

OTHER PUBLICATIONS

Jadhav ("Short oligo (ethylene glycol) functionalized imidazolium dicationic room temperature ionic liquids: Synthesis, properties, and catalytic activity in azidation." Chem Eng J, 200-202, pp. 264-274, online Jun. 19, 2012).*
(Continued)

*Primary Examiner* — Tri V Nguyen
(74) *Attorney, Agent, or Firm* — Knobbe, Martens, Olson & Bear, LLP (57) ABSTRACT

An ionic liquid can disperse graphene at a high concentration. The ionic liquid can be represented by general formula (1):
(Continued)

(1)

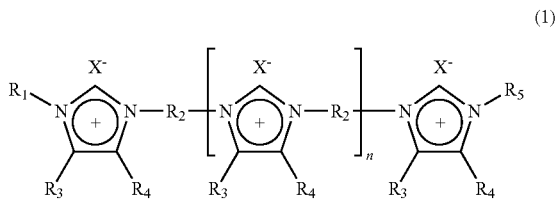

in which $R_1$ and $R_5$ may be the same or different and each independently represents a substituted or unsubstituted C1-7 linear or branched alkyl group; $R_2$ is represented by formula (2):

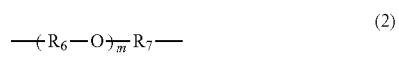

(2)

in which $R_6$ and $R_7$ may be the same or different and each independently represents a C1-4 linear or branched alkylene group, and m represents an integer of 1-5; $R_3$ and $R_4$ may be the same or different and each independently represent a hydrogen atom, substituted or unsubstituted C1-4 linear or branched alkyl group; $X^-$ represents a counter ion; and n represents 0-30.

10 Claims, 4 Drawing Sheets (51) Int. Cl.

| | |
|---|---|
| H01B 1/22 | (2006.01) |
| C09D 5/24 | (2006.01) |
| C07D 233/60 | (2006.01) |
| B82Y 30/00 | (2011.01) |
| B82Y 40/00 | (2011.01) |
| B01F 3/12 | (2006.01) |
| B01F 9/00 | (2006.01) |
| B01F 11/02 | (2006.01) |
| C09K 3/00 | (2006.01) |
| C01B 32/184 | (2017.01) |
| C01B 32/194 | (2017.01) |

(52) U.S. Cl.
CPC .............. *B82Y 30/00* (2013.01); *B82Y 40/00* (2013.01); *C01B 32/184* (2017.08); *C01B 32/194* (2017.08); *C07D 233/60* (2013.01); *C07D 403/14* (2013.01); *C09K 3/00* (2013.01); B01F 2003/125 (2013.01)

(58) Field of Classification Search
CPC ....... H01B 1/04; H01B 1/122; C08L 2666/36; C01B 31/065; C01B 32/182; B82Y 30/00; B82Y 40/00
USPC .................... 252/500–511; 548/313.7, 312.7
See application file for complete search history.

(56) References Cited

U.S. PATENT DOCUMENTS

| | | | |
|---|---|---|---|
| 2012/0157680 A1* | 6/2012 | Watahiki | C07C 309/20 544/178 |
| 2012/0256138 A1 | 10/2012 | Suh | |
| 2012/0261612 A1 | 10/2012 | Suh | |

FOREIGN PATENT DOCUMENTS

| | | | | |
|---|---|---|---|---|
| CN | 1017812353 A | 7/2010 | | |
| EP | 1 555 242 A1 | 7/2005 | | |
| JP | 2004-142972 A | 5/2004 | | |
| JP | 2010-220490 A | 7/2010 | | |
| JP | 2011-219318 | 4/2011 | | |
| KR | 10-2011-0073222 A | 6/2011 | | |
| PL | 202539 B1 | 1/2008 | | |
| WO | WO 9408972 A1 * | 4/1994 | ............. | A01N 43/50 |
| WO | 2011/024988 A1 | 3/2011 | | |

OTHER PUBLICATIONS

Pernak ("Synthesis and Properties of TrigeminalT ricationic Ionic Liquids." Chem—a Europ Journal, 13, pp. 31306-3112, pub 2007).*
Carlisle ("Main-chain imidazolium polymer membranes for CO2 separations: An initial study of a new ionic liquid-inspired platform." J of Memb Sc, 359, pp. 37-43, pub Oct. 22, 2009).*
Schenkel ("New ionic organic compounds containing a linear tris(imidazolium) core and their thermotropic liquid crystal behaviour." Liquid Crystals, Taylor & Francis vol. 40, No. 8, 1067-1081). (Year: 2013).*
Wison ("Resolving Ambiguous Naming for an Ionic Liquid Anion." Chemistry International, vol. 29 No. 4 Jul.-Aug. 2007 (Year: 2007).*
Extended European Search Report dated Dec. 2, 2016 for EP Application 13791216.8.
Lee, W.R. et al. "Electrochemical and optical behavior of bis-imidazolium ionic liquids," Polymer Preprints, 2007, vol. 48, No. 2, pp. 235-236.
Lee, W.R. et al. "Electro-fluorescence switching of bis-imidazolium ionic liquids," Journal of Nanoscience and Nanotechnology, 2008, vol. 8, No. 9, pp. 4630-4634.
Kim, J.Y. et al. "Novel thixotropic gel electrolytes based on dictionic bis-imidazolium salts for quasi-solid-state dye-sensitized solar cells," Journal of Power Sources, 2008, vol. 175, No. 1, pp. 692-697.
Holbrey, J.D. et al. "Mercury (II) partitioning from aqueous solutions with a new, hydrophobic ethylene-glycol functionalized bis-imidazolium ionic liquid," Green Chemistry, 2003, vol. 5, No. 2, pp. 129-135.
Nuvoli, D., et al., "High concentration few-layer graphene sheets obtained by liquid phase exfoliation of graphite in ionic liquid," Journal of Materials Chemistry, 2011, vol. 21, No. 10, pp. 3428-3431.
Novoselov, K.S. et al., "Electric Field Effect in Atomically Thin Carbon Films," Science, 2004, vol. 306 p. 666.
Park, S. and Ruoff, R.S., "Chemical methods for the production of graphenes," Nature nanotec, 2009, vol. 4, 217-224.
Hernandez, Y. et al., "High-yield production of graphene by liquid-phase exfoliation of graphite," Nature Nanotech., 2008, vol. 3, 563-568.
Wang, X. et al., "Direct exfoliation of natural graphite into micrometre size few layers graphene sheets using ionic liquids," Chem. Commun. 2010, vol. 46, pp. 4487-4489.
Anderson, J.L. et al., "Structure and Properties of High Stability Geminal Dicationic Ionic Liquids," J. Am. Chem. Soc., 2005, vol. 127, pp. 593-604.
International Search Report dated Jul. 2, 2013 for PCT/JP2013/063438.
Japanese Office Action, dated Apr. 11, 2017, in Japanese Patent Application No. 2014-515640.
Office Action, dated Dec. 11, 2017, in Korean Patent Application No. 10-2014-7029675.

* cited by examiner

GRAPHENE NANODISPERSION AND METHOD FOR PREPARING SAME

CROSS REFERENCE TO RELATED APPLICATIONS

This application is the U.S. National Phase of International Application No. PCT/JP2013/063438, filed May 14, 2013, designating the U.S. and published in Japanese as WO 2013/172350 on Nov. 21, 2013 which claims the benefit of Japanese Patent Application Nos. 2012-111019, filed May 14, 2012 and 2013-060376, filed Mar. 22, 2013.

TECHNICAL FIELD

The present invention relates to a novel ionic liquid capable of dispersing graphene at a high concentration, a graphene nanodispersion prepared by using the ionic liquid, and a method for preparing the dispersion.

BACKGROUND ART

Graphite, a carbonaceous material, has a layered structure, and one layer thereof is called graphene. Graphene is comprised of only carbon atoms bonded in the form of a hexagonal lattice. It is only one carbon atom thick and has extremely high thermal conductivity. Graphene holds promise as a two-dimensional nanosheet having strikingly excellent electrical conductivity and other electrical properties.

Nobel Prize recipients Geim et al. repeated the following: sticking graphite flakes to adhesive tape, folding the tape so that the adhesive surface of the tape sandwiches the flakes, and pulling the tape apart to peel off the flakes, thereby yielding graphene (Non-patent Reference 1).

In recent years the following two methods have been used as the main methods of producing graphene from graphite: a method for obtaining graphene oxide by exfoliating in water after oxidizing graphite (Non-patent Reference 2) and a method for obtaining graphene dispersed in a liquid by exfoliating graphite in a solvent or surfactant solution using ultrasound or the like (liquid-phase exfoliation) (Non-Patent References 2 and 3).

In the former (graphene oxide) method, graphite powder must first be oxidized using sulfuric acid, sodium nitrate, potassium permanganate, or the like, and a number of steps are required including the subsequent reduction of the graphene oxide. Those processes, strong acid treatment and subsequent short-time ultrasound application, tend to cause structural defects or fragmentation of graphene, which deteriorate the property of graphene (Patent Reference 1). In contrast, the liquid-phase exfoliation of graphite is thought to be a useful method posing no such problems.

The solvent plays an important role for obtaining the maximum yield in the liquid-phase exfoliation. According to recent studies on graphene exfoliation, the theoretical explanation was provided that a solvent effective for graphite exfoliation has a surface tension of approximate 40 mJ/m$^2$ is theoretically explained (Non-patent Reference 2). However, the level of dispersiveness in one-step exfoliation of graphene using ultrasound is about 2 mg/mL at present and is still inadequate for scaling into a wider range of uses.

Various molten salts have been used as solvents for the liquid-phase exfoliation of graphene because of their high dispersion force and many excellent physical properties. Ionic liquids of imidazolium-based salts in particular have been used suitably as media for disentangling carbon nanotube bundles. The interaction between π electrons of the nanotubes and the organic cation is thought to be important for disentanglement and subsequent gelation. Various ionic liquids have been studied in the liquid-phase exfoliation of graphite from this viewpoint, and the maximum concentration of the graphene dispersion reported to date is 5.33 mg/mL (Non-patent Reference 4).

PRIOR ART REFERENCES

Patent References

Patent Reference 1: JP Kokai 2011-219318

Non-Patent References

Non-Patent Reference 1: K. S. Novoselov, A. K. Geim, S. V. Morozov, D. Jiang, Y. Zhang, S. V. Dubonos, I. V. Grigorieva, A. A. Firsov, Science 306 (2004) 666

Non-Patent Reference 2: S. Park, R. S. Ruoff, Nature Nanotech. 4, 217-224 (2009)

Non-Patent Reference 3: Y. Hernandez, V. Nicolosi, M. Lotya, F. M. Blighe, Z. Sun, S. De, I. T. McGovern, B. Holland, M. Byrne, Y. K. Gun'Ko, J. J. Boland, P. Niraj, G. Duesberg, S. Krishnamurthy, R. Goodhue, J. Hutchison, V. Scardaci, A. C. Ferrari, J. N. Coleman, Nature Nanotech. 3, 563-568 (2008)

Non-Patent Reference 4: D. Nuvoli, L. Valentini, V. Alzari, S. Scognamillo, S. B. Bon, M. Piccinini, J. Illescas, A. Mariani, J. Mater. Chem. 21, 3428-3431 (2011)

SUMMARY OF THE INVENTION

The purpose of the present invention is to provide a novel ionic liquid capable of dispersing graphene in a high concentration.

The present inventors focused on viscosity in addition to surface energy as an important factor for dispersiveness while researching solvents to heighten the dispersiveness of graphene. Viscosity is defined as resistance to flow, but the viscosity of a liquid also represents the strength of non-covalent interactions between the solvent molecules. The present inventors discovered that the exfoliation of graphene tends to increase with higher viscosity in known graphene dispersions having approximate surface tension values. They then discovered that a novel ionic liquid that gives a graphene dispersion having a very high concentration can be provided by linking imidazolium-based ionic liquid moieties using an alkylene oxide core and thereby arrived at the present invention.

They also unexpectedly discovered that a graphene dispersion of higher concentration than the case of using the novel ionic liquid alone can be provided by mixing this novel ionic liquid with butylmethylimidazolium hexafluorophosphate (BMIPF$_6$) or butylmethylimidazolium bis(trifluoromethanesulfonyl)imide (C), which has been used in the past as ionic liquids.

Specifically, the present invention provides:

[1] an ionic liquid represented by the following general formula (1):

[Chemical Formula 1]

wherein $R_1$ and $R_5$ may be the same or different and each independently represent a substituted or unsubstituted $C_{1-7}$ linear or branched alkyl group, $R_2$ is represented by the following formula:

[Chemical Formula 2]

wherein $R_6$ and $R_7$ may be the same or different and each independently represent a $C_{1-4}$ linear or branched alkylene group, m represents an integer of 1-5, $R_3$ and $R_4$ may be the same or different and each independently represent a hydrogen atom, substituted or unsubstituted $C_{1-4}$ linear or branched alkyl group, $X^-$ represents a counter ion, n represents 0-30,

[2] the ionic liquid according to [1], wherein $R_1$ and $R_5$ are $C_{1-6}$ linear alkyls,

[3] the ionic liquid according to [1] or [2], wherein $R_6$ and $R_7$ are both ethylene groups,

[4] the ionic liquid according to any of [1]-[3], wherein n is an integer of 0-2,

[5] the ionic liquid according to any of [1]-[4], wherein $X^-$ is selected from $PF_6^-$, $(CF_3SO_2)_2^-N^-$ (or $TFSI^-$), $BF_4^-$, $Cl^-$, and $Br^-$,

[6] an ionic liquid mixture comprising the ionic liquid (A) according to any of [1]-[5] and butylmethylimidazolium hexafluorophosphate (B) or butylmethylimidazolium bis(trifluoromethanesulfonyl)imide (C),

[7] a graphene dispersion containing graphene and the ionic liquid according to any of [1]-[5] or the ionic liquid mixture according to [6],

[8] a method for preparing a graphene dispersion comprising:

(1) a step of adding graphite to the ionic liquid according to any of [1]-[5] or the ionic liquid mixture according to [6], and (2) a step of applying ultrasound or microwaves to the mixture obtained in (1),

[9] the method according to [8], further comprising a step of centrifuging the mixture obtained after application of ultrasound or microwaves, and

[10] the method according to [8] or [9], further comprising a step of recovering a liquid layer from the mixture after centrifugation.

In the present invention, a graphene dispersion having a far higher concentration than in the prior art can be obtained by using, as the solvent, an ionic liquid represented by formula (1) or an ionic liquid mixture of this ionic liquid and BMIPF$_6$. The higher dispersiveness obtained using the ionic liquid of the present invention enables application of graphene to a wider range of uses; for example, to lithium ion secondary batteries and many other such electronic components and energy storage appliances. The method of preparing the graphene dispersion of the present invention also yields good production efficiency and increases industrial value because it enables provision of a high-concentration graphene dispersion by one-step exfoliation of graphite rather than via graphene oxide.

DETAILED DESCRIPTION OF CERTAIN ILLUSTRATIVE EMBODIMENTS

Ionic Liquid

One embodiment of the present invention relates to a novel ionic liquid represented by the following formula (1).

[Chemical Formula 3]

In formula (1), $R_1$ and $R_5$ may be the same or different and each independently represents a substituted or unsubstituted $C_{1-7}$ linear or branched alkyl group. In the present invention, $R_1$ and $R_5$ are preferably $C_{1-6}$ linear alkyl groups, specifically, methyl, ethyl, n-propyl, n-butyl, n-pentyl, or n-hexyl, particularly preferably n-butyl.

In formula (1), $R_2$ is represented by the following formula (2).

[Chemical Formula 4]

Here, $R_6$ and $R_7$ may be the same or different and each independently represent a $C_{1-4}$ linear or branched alkylene group. In the present invention, $R_6$ and $R_7$ are preferably $C_{2-4}$ linear alkylene groups, more preferably ethylene groups.

In formula (2), m is an integer of 1-5, preferably 2 or 3. In the present invention, the moiety represented by formula (2) preferably forms, among others, a triethylene glycol nucleus; i.e., —$CH_2CH_2OCH_2CH_2OCH_2CH_2$—. Without wishing to be bound by theory, the moiety represented by formula (2) in the present invention is also thought to act as a flexible core of an imidazolium salt skeleton having surface tension near 40 mJ/m$^2$ and also to have a role as a hydrogen acceptor. These characteristics are thought to be optimized when this moiety is triethylene glycol.

In formula (1), $R_3$ and $R_4$ may be the same or different and each independently represent a hydrogen atom, substituted or unsubstituted $C_{1-4}$ linear or branched alkyl group. In the present invention, $R_3$ and $R_4$ are preferably both hydrogens.

In formula (1), X$^-$ represents a counter ion, preferably selected from $PF_6^-$, $(CF_3SO_2)_2N^-$, $BF_4^-$, $Cl^-$, and $Br^-$.

In formula (1), n represents 0-30. In the present invention, n is preferably an integer of 0-2; i.e., the imidazolium salt moiety is preferably a dimer, trimer, or tetramer. Since the viscosity increases as n becomes larger, this tends to interfere with ultrasonication and purification to remove the excess graphite remaining in the liquid.

In addition, a continuous synthesis method rather than a sequential synthesis method is used to synthesize the ionic liquid of formula (1) when n is large. In this case, the ionic liquid of formula (1) is a mixture of compounds having n of various numbers, and n is indicated as the average of these values. The present invention also encompasses cases in which an ionic liquid represented by formula (1) is such a mixture.

An example of a method of synthesizing an ionic liquid represented by formula (1) is shown below.
[Chemical Formula 5]

Scheme 1 is a scheme for synthesizing compound 1 in which the imidazolium salt moiety is a dimer (when n=0). Synthesis is performed, for example, as follows.

1-Butylimidazole is added to an acetonitrile solution of triethylene glycol bis(p-toluenesulfonic acid ester) under an argon atmosphere, heated, and mixed. The reaction mixture is concentrated under reduced pressure and dried. Methylene chloride etc. is added to the viscous residue, and two-layer separation is carried out by ethyl acetate or the like. Then, the ionic liquid layer is dried with a rotary evaporator and a vacuum oven to obtain Compound 1a, which is a pale yellow, viscous liquid. Next, an aqueous solution of $KPF_6$ is added to an acetonitrile solution of compound 1a and the obtained mixture is stirred at room temperature, thereby separating the reaction mixture into a water layer and an ionic liquid layer. The ionic liquid is washed with methylene chloride or the like and dried to obtain compound 1, which is a viscous liquid.

An ionic liquid can also be synthesized by continuous synthesis method when n in formula (1) is large. An example is shown below.

Scheme 2 is an example of a method for producing an ionic liquid by continuous synthesis method. Compound 4 obtained here is a mixture of compounds of n of various numbers, and n is indicated as the average of these values.

[Chemical Formula 6]

Compound 4

An acetonitrile solution of compound B (1,1'-[1,2-ethanediylbis(oxy-2,1-ethanediyl)]bis(imidazole)) and triethylene glycol bis(p-toluenesulfonic acid ester) are heated and stirred under an argon atmosphere. Compound B can be synthesized based on J. E. Bara. Ind. Eng. Chem. Res. 50, 13614 (2011). 1-Butylimidazole is then added to the reaction mixture, the combination is stirred, and an aqueous solution of $KPF_6$ is added. The reaction mixture is stirred further, and this mixture is separated into a water layer and an ionic liquid layer. The supernatant water layer is transferred, and the ionic liquid layer is washed by distilled water, dried, extracted by acetic acid or the like, then concentrated using a rotary evaporator, and compound 4 is obtained by drying overnight in a vacuum oven at 105° C. using $P_2O_5$.

Ionic Liquid Mixture

Another embodiment of the present invention relates to an ionic liquid mixture comprising an ionic liquid (A) represented by formula (1) and butylmethylimidazolium hexafluorophosphate (B) or butylmethylimidazolium bis(trifluoromethanesulfonyl)imide (C).

Any ionic liquid represented by formula (1) can be used as A in the ionic liquid mixture of the present invention. However, an ionic liquid is especially preferred in which $R_2$ in formula (1) is a triethylene glycol or tetraethylene glycol group and n is 0-2.

The volume ratio of A and B in an ionic liquid mixture of the present invention varies depending on the type of ionic liquid of A. For example, when A is an ionic liquid containing a compound in which the imidazolium salt moiety is a dimer (n =0 in formula (1)), A may range greater than 0 and less than 1.0 and B may range less than 1.0 and greater than 0. When A is an ionic liquid in which the imidazolium salt moiety is a tetramer (n=2 in formula (1)), A is greater than 0 and less than 1.0 and B is less than 1.0 and greater than 0.

In addition to A and B or C, other solvents, for example, methanol, water, and the like, may be added as appropriate in the ionic liquid mixture of the present invention.

Graphene Dispersion and Method for Preparing Same

Another embodiment of the present invention relates to a graphene dispersion containing graphene and the ionic liquid or ionic liquid mixture of the present invention. Graphene is dispersed in a high concentration in the graphene dispersion of the present invention. Graphene typically has a layered distribution and is often a mixture of single-layered graphene and multiple-layered graphene. In the present specification, "graphene" includes not only single-layered graphene but also graphene having multiple layers, preferably 9 or fewer layers stacked.

The graphene dispersion of the present invention preferably contains 10 mg or more, more preferably 20 mg or more, and even more preferably 40 mg or more, of graphene per milliliter of dispersion. A dispersion containing such a high concentration of graphene can be provided for the first time by the present invention. The graphene dispersion of the present invention can be prepared, for example, by a method such as the following, but not by way of limitation thereto.

The method for preparing a graphene dispersion in the present invention includes a step of adding graphite to an ionic liquid represented by formula (1); or an ionic liquid mixture containing this ionic liquid and butylmethylimidazolium hexafluorophosphate or butylmethylimidazolium bis (trifluoromethanesulfonyl)imide, and a step of applying ultrasound or microwaves to the mixture obtained.

Graphite particles that can be used in the preparation method of the present invention have an average particle size of 100 μm or less, preferably from 1 μm to 100 μm. Here, the average particle size is the value of the particle diameter $d_{50}$ at 50% in the cumulative distribution.

Any ultrasonic disperser can be used in the present invention, but a horn-type ultrasonic disperser is preferably used. The frequency of the ultrasound is from about 10 kHz to 1 MHz. The amplitude of the ultrasound is from about 1 μm to 100 μm (zero to peak value). The ultrasound application time is not particularly restricted, but is usually one minute or more, preferably from one minute to six hours.

Any microwave oven can also be used in the present invention. For example, an ordinary 500 W, 2.4 GHz microwave oven can be used. The duration of microwave application is not particularly restricted, but is usually 10 seconds or longer, preferably from 10 seconds to 10 minutes.

Low-energy microwaves of, for example, 1-100 W, 2.4 GHz, can also be applied in the present invention. In this case, the duration is about 0.2-48 hours.

The method for preparing a graphene dispersion of the present invention may also include a step of centrifuging the liquid after applying ultrasound and may also include a step of recovering the liquid layer from the mixture after centrifugation. In this case, the entire amount or part, for example, of the mixture obtained after ultrasound application is centrifuged using a centrifuge, and a graphene dispersion is obtained by collecting the supernatant. The centrifugation conditions can be adjusted as appropriate depending on the desired graphene concentration.

EXAMPLES

The present invention is described through examples below, but the present invention is not limited thereto.

A. Synthesis of Ionic Liquid

Synthesis Example 1

Compound 1 of the present invention was synthesized by the following procedure.
[Chemical Formula 7]

(1) Synthesis of Compound 1a

1-Butylimidazole (37.15 g, 0.299 mol) was added to an acetonitrile solution (40 mL) of triethylene glycol bis(p-toluenesulfonic acid ester) (62.36 g, 0.136 mol) under an argon atmosphere, and the mixture was mixed for 72 hours at 60° C. The reaction mixture was concentrated under reduced pressure and dried, and methylene chloride (10 mL) was added to the viscous residue. Two-layer separation was carried out three times with ethyl acetate (50 mL). Compound 1a (57 g, 0.129 mol, yield: 81%), which is a pale yellow, viscous liquid, was obtained when the ionic liquid layer was dried by a rotary evaporator and by a vacuum oven overnight at 105° C. using $P_2O_5$.

$^1$HNMR (500 MHz, DMSO-d6, 25° C.) d(ppm) 9.17 (s, 2H), 7.81(t, J=1.5 Hz, 2H), 7.74(t, J=1.5 Hz, 2H), 7.48(d, J=8.5 Hz, 4H), 7.12(d, J=7.9 Hz, 4H), 4.33(t, J=4.9 Hz, 4H), 4.17(t, J=7.0 Hz, 4H), 3.73(t, J=4.9 Hz, 4H), 3.51(s, 4H), 2.29(s, 6H), 1.75(dt, J=15.0, 7.0 Hz, 4H), 1.22(t d, J=15.0, 7.5 Hz, 4H), 0.88(t, J=7.3 Hz, 6H); $^{13}$CNMR (125 MHz, DMSO-d6, 25° C.) d(ppm) 145.7, 137.6, 136.3, 125.5, 122.8, 122.3, 69.3, 68.1, 48.7, 48.5, 31.3, 20.8, 18.7, 13.2; ESI-MS: m/z535.29([M-OT$_s$]+calcd. for $C_{27}H_{43}N_4O_5S$+ 535.30)

(2) Synthesis of Compound 1

An aqueous solution of $KPF_6$ (23 g, 0.125 mol) was added to an acetonitrile solution (30 mL) of compound 1a (38.17 g, 0.054 mol), and the mixture was stirred for two hours at room temperature. The reaction mixture separated into a water layer and an ionic liquid layer. The supernatant water layer was transferred, 10 mL of methylene chloride was added, and the ionic liquid layer was washed three times with distilled water (30 mL). Compound 1 (30.3 g, 0.046 mol, yield: 85%), which is a viscous liquid, was obtained by drying the ionic liquid layer by $Na_2SO_4$, concentrating using a rotary evaporator, and drying overnight in a vacuum oven at 105° C. with $P_2O_5$.

$^1$HNMR(500 Mhz, DMSO-d6, 25° C.) d(ppm) 9.13 (s, 2H), 7.79 (t, J=1.8 Hz, 2H), 7.72(t, J=1.8 Hz, 2H), 4.33(t, J=4.9 Hz, 4H), 4.18(t, J=7.0 Hz, 4H), 3.74(t, J=5.2 Hz, 4H), 3.52(s, 4H), 1.77(dt, J=15.3, 6.9 Hz, 4H), 1.25(t d, J=15.0, 7.3 Hz, 4H), 0.90(t, J=7.3 Hz, 6H); $^{13}$CNMR(125 MHz, DMSO-d6, 25° C.) d(ppm) 136.3, 122.8, 122.2, 69.3, 68.1, 48.8, 48.6, 31.3, 18.7, 13.2; ESI-MS:m/z509.25([M-$PF_6$]+, calcd. for $C_{20}H_{36}F_6N_4O_2P$+509.25).

Synthesis Example 2

Compound 2 of the present invention was synthesized by the following procedure.

[Chemical Formula 8]

(1) Synthesis of Compound 2

An aqueous solution of lithium bis(trifluoromethanesulfonyl)imide (35 g, 0.122 mol) was added to an acetonitrile solution (20 mL) of compound 1a (36.78 g, 0.052 mol) obtained in Synthesis Example 1 under an argon atmosphere, and the mixture was stirred for two hours at room temperature. The reaction mixture separated into a water layer and an ionic liquid layer. The supernatant water layer was transferred, 10 mL of methylene chloride was added, and the ionic liquid layer was washed three times with distilled water (30 mL). A yellow liquid (44.5 g, 0.048 mol, yield: 92%) was obtained by drying the ionic liquid layer with $Na_2SO_4$, concentrating using a rotary evaporator, and drying overnight in a vacuum oven at 105° C. using $P_2O_5$.

$^1$HNMR(500 MHz, DMSO-d6, 25° C.) d(ppm) 9.13 (s, 2H), 7.79 (t, J=1.8 Hz, 2H), 7.72(t, J=1.5 Hz, 2H), 4.33(t, J=4.9 Hz, 4H), 4.19(t, J=7.3 Hz, 4H), 3.74(t, J=5.2 Hz, 4H), 3.53(s, 4H), 1.77(dt, J=15.3, 7.0 Hz, 4H), 1.25(t d, J=15.0, 7.5 Hz, 4H), 0.90(t, J=7.6 Hz, 6H); $^{13}$CNMR(125 MHz, DMSO-d6, 25° C.) d(ppm) 136.3, 122.8, 122.2, 69.3, 68.1, 48.8, 48.6, 31.3, 18.7, 13.2; ESI-MS:m/z644.19([M-TFSI]+ calcd. for $C_{22}H_{36}F_6N_5O_6S_2$+644.20).

Synthesis Example 3

Compound 3 of the present invention was synthesized by the following procedure.

[Chemical Formula 9]

(1) Synthesis of compound A 1-Butylimidazole (4.69 g, 0.038 mol) was added to an acetonitrile solution (60 mL) of triethylene glycol bis(p-toluenesulfonic acid ester) (52 g, 0.113 mol) under an argon atmosphere, and the mixture was stirred for 10 hours at 60° C. The reaction mixture was concentrated under reduced pressure, dried, and methylene chloride (15 mL) was added to the viscous residue. Compound A (15 g, 0.026 mol, yield: 68%) was obtained as a pale yellow, viscous liquid by purifying the residue by silica column chromatography (methylene chloride/methanol=9/1).

$^1$HNMR(500 MHz, DMSO-d6, 25° C.) d(ppm) 9.13(s, 1H), 7.76(dd, J=13.4, 7.9 Hz, 4H), 7.48(dd, J=7.6, 5.8 Hz, 4H), 7.11(d, J=7.9 Hz, 2H), 4.33(t, J=4.9 Hz, 2H), 4.17(t, J=7.0 Hz, 2H), 4.10(t, J=4.6 Hz, 3H), 3.75(t, J=4.9 Hz, 2H), 3.55(t, J=4.3 Hz, 2H), 3.49(t, J=2.7 Hz, 2H), 3.45(t, J=2.7 Hz, 2H), 3.34(s, 4H), 2.42(s, 3H), 2.29(s, 3H), 1.75(d t, J=15.3, 7.0 Hz, 2H), 1.24(td, J=15.0, 7.3 Hz, 2H), 0.89(t, J=7.3 Hz, 3H); $^{13}$CNMR(125 MHz, DMSO-d6, 25° C.) d(ppm) 145.82, 144.98, 137.52, 136.27, 132.31, 130.16, 128.02, 127.59, 125.47, 122.79, 122.21, 69.95, 69.50, 69.37, 68.08, 67.88, 48.77, 48.58, 48.53, 31.32, 21.08, 20.76, 18.74, 13.24; ESI-MS:m/z411.19 [M-OT$_s$]+ calcd. for $C_{20}H_{31}N_2O_5S$+411.20)

(2) Synthesis of Compound B

Compound B (1,1'-[1,2-ethanediylbis(oxy-2,1-ethanediyl)]bis(imidazole)) was synthesized based on J. E. Bara. Ind. Eng. Chem. Res. 50, 13614 (2011).

(3) Synthesis of Compound 3a

A mixture of compound A (13.85 g, 0.024 mol) and compound B (2.97 g, 0.012 mol) was stirred for 48 hours at 60° C. in acetonitrile under an argon atmosphere. Compound 3a (16.82 g, 0.012 mol, yield: 100%) was obtained as a pale yellow, viscous liquid by concentrating the reaction mixture using a rotary evaporator and dried overnight in a vacuum oven at 105° C. using $P_2O_5$.

$^1$HNMR(500 MHz, DMSO-d6, 25° C.) d(ppm) 9.17(s, 2H), 9.14(s, 2H), 7.80(t, J=1.8 Hz, 2H), 7.74(dd, J=4.9, 1.8 Hz, 6H), 7.48(d, J=7.9 Hz, 8H), 7.11(d, J=7.9 Hz, 8H), 4.34(td, J=9.0, 4.5 Hz, 12H), 4.17(t, J=7.0 Hz, 4H), 3.73(t, J=4.9 Hz, 12H), 3.51(d, J=1.2 Hz, 12H), 2.29(s, 12H), 1.74(dt, J=15.4, 7.0 Hz, 4H), 1.22(td, J=15.0, 7.5 Hz, 4H), 0.88(t, J=7.3 Hz, 6H); $^{13}$CNMR(125 MHz, DMSO-d6. 25° C.) d(ppm) 145.68, 137.65, 136.62, 136.32, 128.07, 125.46, 122.78, 122.61, 122.26, 69.32, 68.18, 68.09, 48.71, 48.52, 31.35, 20.77, 18.73, 13.25; ESI-MS: m/z1243.54([M-OT$_s$]+ calcd. for $C_{59}H_{87}N_8O_{15}S_3$+1243.55)

(3) Synthesis of Compound 3

An aqueous solution of KPF$_6$ (9.97 g, 0.054 mol) was added to an acetonitrile solution (10 mL) of compound 3a (16.82 g, 0.012 mol), and the mixture was stirred for two hours at room temperature. The supernatant water layer was transferred from the reaction mixture, and the ionic liquid was washed three times with distilled water (30 mL). The ionic liquid layer was dried by Na$_2$SO$_4$ and concentrated using a rotary evaporator. Compound 3 (14.78 g, 0.011 mol, yield: 94%) was then obtained as a yellow, viscous liquid by drying this liquid overnight in a vacuum oven at 105° C. using $P_2O_5$.

$^1$HNMR(500 MHz, DMSO-d6, 25° C.) d(ppm) 9.12 (s, 2H), 9.07(s, 2H), 7.79(t, J=1.5 Hz, 2H), 7.72(dd, J=3.4, 1.5 Hz, 6H), 4.36-4.32(m, 12H), 4.18(t, J=7.0 Hz, 4H), 3.74(t, J=4.9 Hz, 12H), 3.53(t, J=2.4 Hz, 12H), 1.77(dt, J=15.0, 6.9 Hz, 4H), 1.25(td, J=14.8, 7.5 Hz, 4H), 0.90(t, J=7.3 Hz, 6H); $^{13}$CNMR(125 MHz, DMSO-d6, 25° C.) d(ppm) 136.52, 136.25, 122.78, 122.60, 122.26, 69.29, 68.17, 68.08, 48.74, 48.56, 31.33, 18.73, 13.24; ESI-MS: m/z1165.40 ([M-PF$_6$]+ calcd. for $C_{38}H_{66}F_{18}N_8O_6P_3$+1165.40)

B. Evaluation of the Dispersiveness of the Ionic Liquid of the Present Invention (1) Preparation of a Graphene Dispersion Seven hundred milligrams of graphite (STG0561 (purity: 98%, average particle size: approximately 45 μm) manufactured by Wako Pure Chemical Industries, Ltd.) was dispersed in 10 mL of ionic liquid or ionic liquid mixture and mixed uniformly for 15 minutes by grinding in a mortar. Ultrasound was applied for four hours at 175 W to the black paste using a horn-type ultrasonic disperser (VCX-500 manufactured by Sonics, 500 W). The dispersion obtained was centrifuged for 30 minutes at 18,000 g, and the graphite was removed to isolate a graphene dispersion.

(2) Calculation of Graphene Concentration

The graphene concentration in the dispersion was measured by vacuum filtering 0.2 mL of a graphene dispersion by a PTFE membrane (pores: 0.1 μm, diameter: 25 mm) manufactured by Advantec. The amount of graphene in the dispersion was calculated by weighing the membrane before use, thoroughly washing the membrane with acetonitrile (50 mL) and dichloromethane (50 mL) after filtration, drying for one hour at 70° C. in a vacuum oven, and weighing the dried membrane.

Example 1

Figure 1:
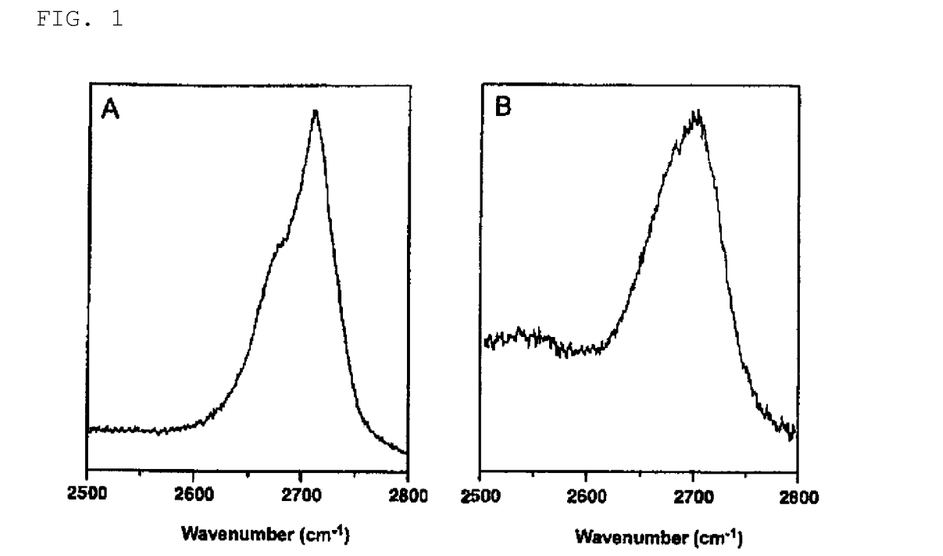
FIG. 1 Raman spectrum of graphene powder obtained from a graphene dispersion using graphite powder and the ionic liquid (compound 1) of the present invention.

A graphene dispersion of compound 1 was prepared by the above procedure and was confirmed to contain graphene in a concentration of 12.29 mg/mL by calculating the graphene concentration. FIG. 1 shows Raman spectra of graphite powder and the graphene powder obtained from the above dispersion. A is the spectrum of the graphite powder, and B is the spectrum of the graphene powder. The change in the shape of the two-dimensional peak is due to disordered graphene which is not layered.

Comparative Example 1

The same experiment as in Example 1 was carried out using butylmethylimidazolium hexafluorophosphate as the dispersant. The dispersion obtained was confirmed to contain graphene in a concentration of 5.33 mg/mL.

C. Evaluation of the Dispersiveness of an Ionic Liquid Mixture of the Present Invention Example 2

Ionic liquid mixtures were prepared by mixing compound 1 and butylmethylimidazolium hexafluorophosphate (BMIPF$_6$) in ratios of 0:100, 35:65, 56:44, 70:30, and 100:0 (volume ratio). The same experiment as in Example 1 was carried out using these ionic liquid mixtures as the dispersant. Table 1 shows the results of measurement of the graphene concentrations of the dispersions obtained.

Example 3

Ionic liquid mixtures were prepared by mixing compound 3 and BMIPF$_6$ in ratios of 0:100, 35:65, 56:44, 70:30, and 100:0 (volume ratio). The same experiment as in Example 1 was carried out using these ionic liquid mixtures as the dispersant. Table 1 shows the results of measurement of the graphene concentrations of the dispersions obtained.

TABLE 1

| | Ionic liquid:BMIPF$_6$ (volume ratio) | | | | |
|---|---|---|---|---|---|
| | 0:100 | 35:65 | 56:44 | 70:30 | 100:0 |
| Graphene concentration when compound 1 was used as ionic liquid | 1 | 18 | 23 | 25 | 12 |
| Graphene concentration when compound 3 was used as ionic liquid | 1 | 41 | 45 | 30 | NA |

Graphene concentrations in table: mg/mL

As described above, the use of the novel ionic liquid of the present invention enables provision of a high-concentration graphene dispersion. It was also found that ionic liquid mixtures containing the novel ionic liquid of the present invention and BMIPF$_6$ enables provision of a graphene dispersion of a higher concentration than the case of using the novel ionic liquid of the present invention alone.

D. Evaluation of the Distribution of Number of Graphene Layers

The distribution of number of graphene layers in a dispersion can be studied by measuring the Raman spectrum of a graphene dispersion by the method described in Nat. Mat. 2012, 11, 217, and assessing the position of a Raman peak derived from 2D band in 2600-2800 cm$^{-1}$.

Figure 2:
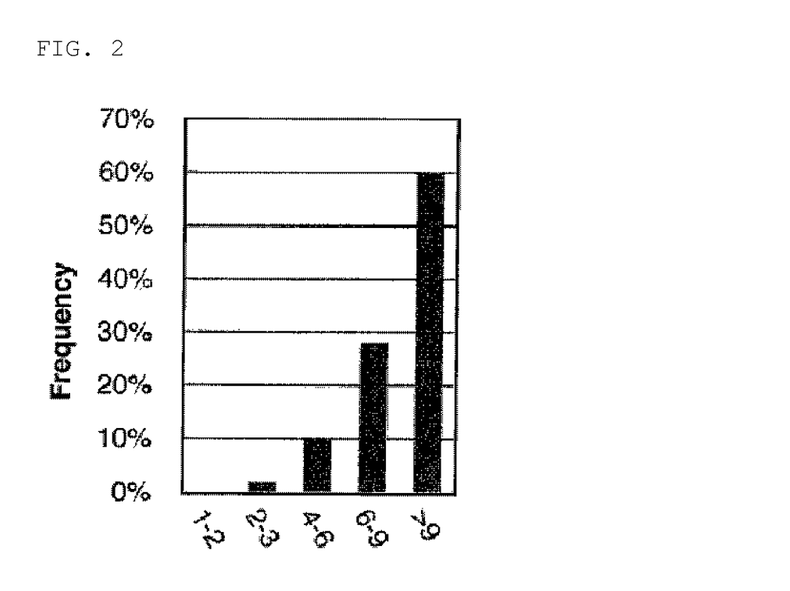
FIG. 2 Distribution of number of graphene layers in graphite.

FIG. 2 shows the distribution of number of graphene layers of graphite obtained by measuring the Raman spectrum by adding graphite to acetonitrile, without ultrasonication or centrifugation. It is evident from FIG. 2 that graphene having more than 9 layers accounts for 60% or more in graphite not subjected to any particular dispersion treatment.

The distribution of number of graphene layers was studied using the ionic liquids of the present invention in the following examples.

Example 4

Figure 3:
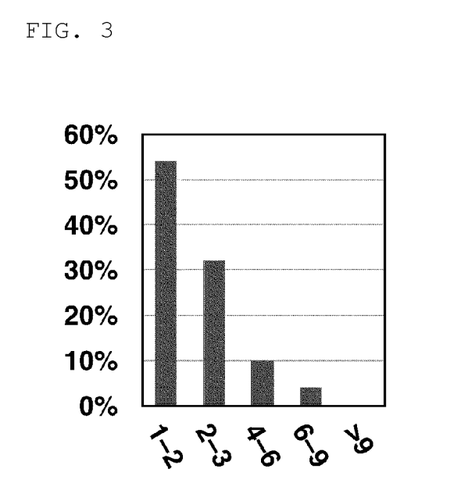
FIG. 3 Distribution of number of graphene layers in a graphene dispersion obtained by microwave treatment using compound 1.

To an ionic liquid of compound 1, graphite was added so as to prepare a graphite mixture of a concentration of 100 mg/mL. A graphene dispersion was obtained by applying microwaves to this mixture for 30 seconds under conditions of 100 W, 2.4 GHz using a microwave reactor CEM Discovery. FIG. 3 shows the results obtained by studying the distribution of number of graphene layers of the graphene dispersion obtained.

Figure 4:
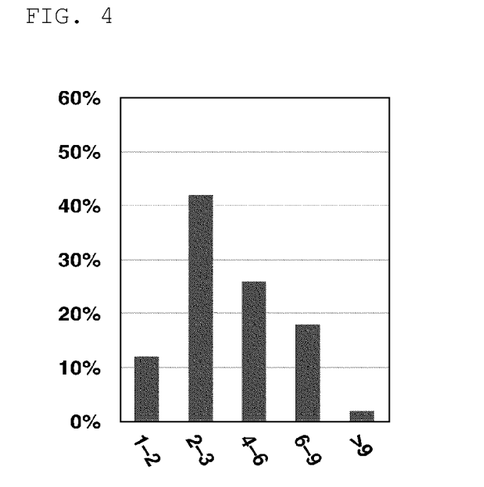
FIG. 4 Distribution of number of graphene layers in a graphene dispersion obtained by ultrasonication using compound 1.

FIG. 4 shows the results obtained by studying the distribution of number of graphene layers of a graphene dispersion obtained by applying ultrasound for one hour to the above mixture.

FIG. 3 shows that short-term microwave treatment increases the proportion of graphene with 1-2 layers to 50% or higher.

Example 5

Figure 5:
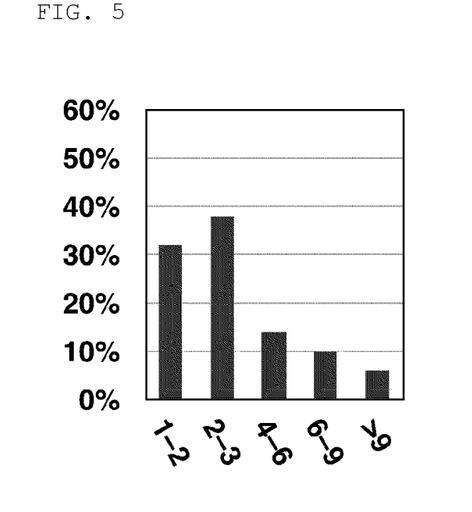
FIG. 5 Distribution of number of graphene layers in a graphene dispersion obtained by microwave treatment using compound 3.

A graphene dispersion was obtained by applying microwaves to a graphite mixture in the same way as in Example 4 using an ionic liquid of compound 3. FIG. 5 shows the results obtained by studying the distribution of number of graphene layers of the graphene dispersion obtained.

Comparative Example 1

Figure 6:
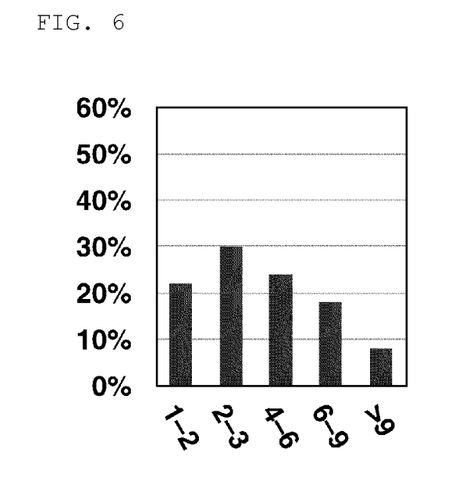
FIG. 6 Distribution of number of graphene layers in a graphene dispersion obtained by microwave treatment using BMIPF$_6$.

A graphene dispersion was obtained by applying microwaves to a graphite mixture in the same way as in Example 4 using BMIPF$_6$. FIG. 6 shows the results obtained by studying the distribution of number of graphene layers of the graphene dispersion obtained.

FIGS. 4 and 5 suggest that microwave treatment can serve as effective means for obtaining a graphene dispersion when using the ionic liquid of the present invention.

E. Preparation of a Graphene Dispersion by Microwave Treatment

Example 6

Next, a study was made as to whether a graphene dispersion can be prepared by applying lower-energy microwaves.

Figure 7:
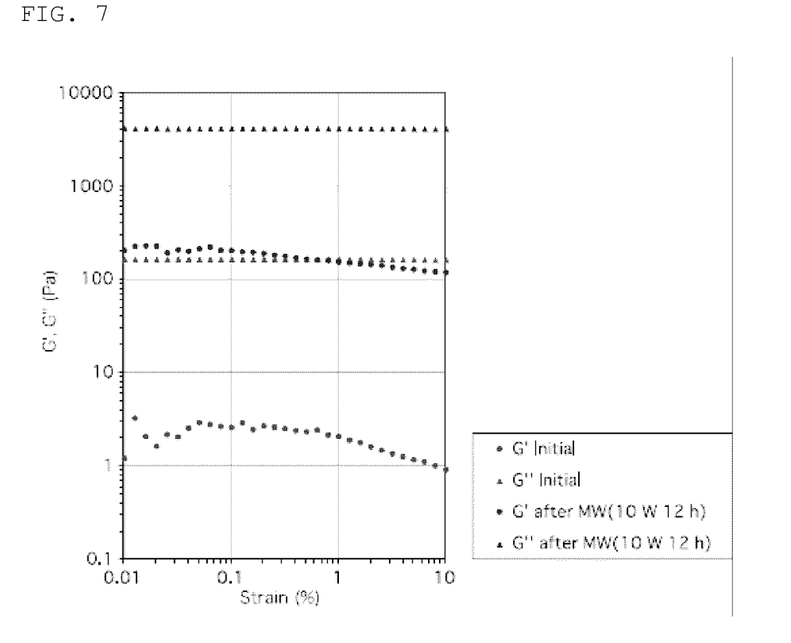
FIG. 7 Dynamic viscoelastic properties of a dispersion before and after microwave treatment using compound 1.

To an ionic liquid of compound 1, graphite was added so as to prepare a graphite mixture of a concentration of 100 mg/mL. Microwaves were applied to this mixture for 12 hours under conditions of 10 W, 2.4 GHz using a microwave reactor CEM Discovery. The dynamic viscoelasticity of the dispersion obtained was measured. The results are shown in FIG. 7.

In the dispersion obtained by applying microwaves, G' representing the storage modulus and G" representing the loss modulus both increase about 50-fold in comparison to the initial stage (before the microwave application). This shows that entanglement of graphene occurs due to loss of the layered structure of the graphite and exfoliation of layers, resulting in a rise in viscosity.

It is therefore demonstrated that the use of the ionic liquid of the present invention enables preparation of a graphene dispersion even by applying low-energy microwaves.

Thus, the high dispersiveness obtained by the ionic liquid of the present invention facilitates to make graphene into a film and enables application of graphene to many electronic components such as lithium ion secondary batteries and in energy storage appliances. The production method of the present invention also has good production efficiency and is of great industrial value as it enables provision of a high-concentration graphene dispersion by one-step exfoliation of graphite rather than via graphene oxide.

What is claimed is:

1. An ionic liquid represented by the following general formula (1):

(1)

wherein R$_1$ and R$_5$ may be the same or different and each independently represent a substituted or unsubstituted C$_{1-7}$ linear or branched alkyl group,
R$_2$ is represented by the following formula (2):

(2)

wherein $R_6$ and $R_7$ may be the same or different and each independently represent a $C_{1-4}$ linear or branched alkylene group, m represents an integer of 2 or 3, $R_3$ and $R_4$ may be the same or different and each independently represent a hydrogen atom, substituted or unsubstituted $C_{1-4}$ linear or branched alkyl group, $X^{31}$ represents a counter ion, n represents 1-30.

2. The ionic liquid according to claim 1, wherein $R_1$ and $R_5$ are $C_{1-6}$ linear alkyls.

3. The ionic liquid according to claim 1, wherein $R_6$ and $R_7$ are both ethylene groups.

4. The ionic liquid according to claim 1, wherein n is an integer of 1-2.

5. The ionic liquid according to claim 1, wherein $X^-$ is selected from the group consisting of $PF_6^-$, $(CF_3SO_2)_2N^-$, $BF_4^-$, $Cl^-$, and $Br^-$.

6. An ionic liquid mixture comprising the ionic liquid (A) according to claim 1 and butylmethylimidazolium hexafluorophosphate (B) or butylmethylimidazolium bis(trifluoromethanesulfonyl)imide (C).

7. A graphene dispersion comprising graphene and the ionic liquid according to claim 1 or an ionic liquid mixture comprising the ionic liquid (A) according to claim 1 and butylmethylimidazolium hexafluorophosphate (B) or butylmethylimidazolium bis(trifluoromethanesulfonyl)imide (C).

8. A method for preparing a graphene dispersion comprising:
   (1) adding graphite to the ionic liquid according to claim 1 or an ionic liquid mixture comprising the ionic liquid (A) according to claim 1 and butylmethylimidazolium hexafluorophosphate (B) or butylmethylimidazolium bis(trifluoromethanesulfonyl)imide (C), and
   (2) applying ultrasound or microwaves to the mixture obtained in (1).

9. The method according to claim 8, further comprising centrifuging the mixture obtained after application of ultrasound or microwaves.

10. The method according to claim 8, further comprising recovering a liquid layer from the mixture after centrifugation.

* * * * *